(12) United States Patent
Nishimura et al.

(10) Patent No.: US 7,045,061 B2
(45) Date of Patent: May 16, 2006

(54) DIALYSIS DEVICE

(75) Inventors: Takayuki Nishimura, Ishikawa-Ken (JP); Yoichi Itoh, Ishikawa-Ken (JP)

(73) Assignee: Shibuya Kogyo Co., Ltd., Kanazawa (JP)

( * ) Notice: Subject to any disclaimer, the term of this patent is extended or adjusted under 35 U.S.C. 154(b) by 205 days.

(21) Appl. No.: 10/844,876

(22) Filed: May 13, 2004

(65) Prior Publication Data

US 2004/0262203 A1     Dec. 30, 2004

(30) Foreign Application Priority Data

Jun. 30, 2003   (JP)   ............................ 2003-188111

(51) Int. Cl.
*B01D 61/26* (2006.01)
*B01D 61/28* (2006.01)

(52) U.S. Cl. .............. 210/321.71; 210/252; 210/257.1; 210/257.2; 210/258; 210/416.1

(58) Field of Classification Search ................ 210/252, 210/257.1, 257.2, 258, 321.65, 321.71, 416.1; 417/397, 404
See application file for complete search history.

(56) References Cited

U.S. PATENT DOCUMENTS 4,267,040 A * 5/1981 Schal .......................... 210/104

FOREIGN PATENT DOCUMENTS

JP           3395872         2/2003

* cited by examiner

*Primary Examiner*—John Kim
(74) *Attorney, Agent, or Firm*—Flynn, Thiel, Boutell & Tanis, P.C.

(57) ABSTRACT

A dialysis device 1 includes a water supply passage 15 for supplying clean water to solution supply chambers 35a and 35b, and a waste solution passage for discharging a used dialysis solution from solution collection chambers 34a and 34b, and the water supply passage includes a concentrate solution pump 21 that supplies a dialysis concentrate solution from concentrate solution supply source 19. The concentrate solution pump is a piston pump 40 that moves a piston 42 up and down in a cylinder 41 to feed a solution, the piston pump is provided in the way of washing passage 26 provided between the water supply passage and the waste solution passage, and an open/close valve 27 that intermittently opens and closes is provided in the washing passage to flow the clean water in the water supply passage through a gap between the cylinder and the piston.

3 Claims, 4 Drawing Sheets

DIALYSIS DEVICE

FIELD OF THE INVENTION

The present invention relates to a dialysis device, and more particularly to a dialysis device having a piston pump.

DESCRIPTION OF THE PRIOR ART

Dialysis devices have used a piston pump that moves a piston up and down in a cylinder to feed a solution, as a extraction pump for feeding a dialysis solution (Patent Document 1: Japanese Patent No. 3395872).

It is known that when a dialysis solution is fed by a piston pump, a deposition from the dialysis solution may cause adhesion between a cylinder and a piston. In this connection, Patent Document 1 discloses that in order to prepare a dialysis solution by mixing a dialysis concentrate solution and water, a single-patient-use dialysis device includes a supply line of water for diluting the dialysis concentrate solution, and thus a deposition that causes adhesion between a cylinder and a piston can be washed off even during dialysis by providing washing ports in a extraction pump of the single-patient-use dialysis device, connecting the supply line of water to the ports, and flowing water into a port on an inflow side and flowing the water out of a port on an outflow side.

However, as disclosed in Patent Document 1, when the supply line of water is simply connected to the washing ports of the piston pump for flowing water into the pump, water supply pressure from a water supply source to the supply line always acts between the cylinder and the piston of the piston pump, and the water having flown into the pump may leak into a metering chamber that sucks a dialysis solution in the cylinder or out of the piston pump.

Further, if such a piston pump is used as a concentrate solution pump for dispensing a dialysis concentrate solution, water leaking into the metering chamber may dilute the dialysis concentrate solution.

SUMMARY OF THE INVENTION

In view of the above described problems, the invention provides a dialysis device that prevents impairment of sliding performance between sliding portions of a piston and a cylinder of a piston pump, and prevents a leak of water from the sliding portions caused by water supply pressure.

Specifically, the invention provides a dialysis device including: a solution supply chamber for supplying a new dialysis solution to a dialyser via a supply passage; a solution collection chamber for collecting a used dialysis solution from the dialyser via a collection passage; a water supply passage for supplying clean water to the solution supply chamber; a waste solution passage for discharging the used dialysis solution from the solution collection chamber; and a piston pump that moves a piston up and down in a cylinder to feed a solution, wherein the dialysis device further includes: a washing passage that provides communication between the water supply passage and the waste solution passage to flow the clean water therethrough; and an open/close valve for opening and closing the washing passage, and the piston pump is at least one of a concentrate solution pump that sucks a dialysis concentrate solution from a concentrate solution supply source and supplies the sucked concentrate solution to the solution supply chamber, and a extraction pump that sucks the used dialysis solution from the collection passage and discharges the sucked used dialysis solution to the waste solution passage, the cylinder of the piston pump has an inflow port for flowing a solution into a gap between an inner surface of the cylinder and an outer surface of the piston, and an outflow port for flowing the solution out of the gap, and the inflow port and the outflow port are connected in the way of the washing passage, and the open/close valve is intermittently opened during a dialysis operation to flow the clean water in the water supply passage through the gap between the inner surface of the cylinder and the outer surface of the piston.

According to the invention, the clean water from the water supply passage is flown through the gap between the piston and the cylinder to wash off the used dialysis solution having flown into the gap between the piston and the cylinder when the piston pump is the extraction pump, and to prevent drying of the dialysis concentrate solution having flown into the gap between the piston and the cylinder when the piston pump is the concentrate solution pump, thereby preventing impairment of sliding performance between the piston and the cylinder.

Further, the open/close valve is intermittently opened, and thus water supply pressure of the clean water having flown into the inflow port intermittently acts between the cylinder and the piston. This prevents a leak of the clean water into a metering chamber of the piston pump to keep the amounts of dialysis solution and concentrate solution with high accuracy, and prevents a leak of the clean water out of the piston pump.

DETAILED DESCRIPTION OF THE EMBODIMENTS

Figure 1:
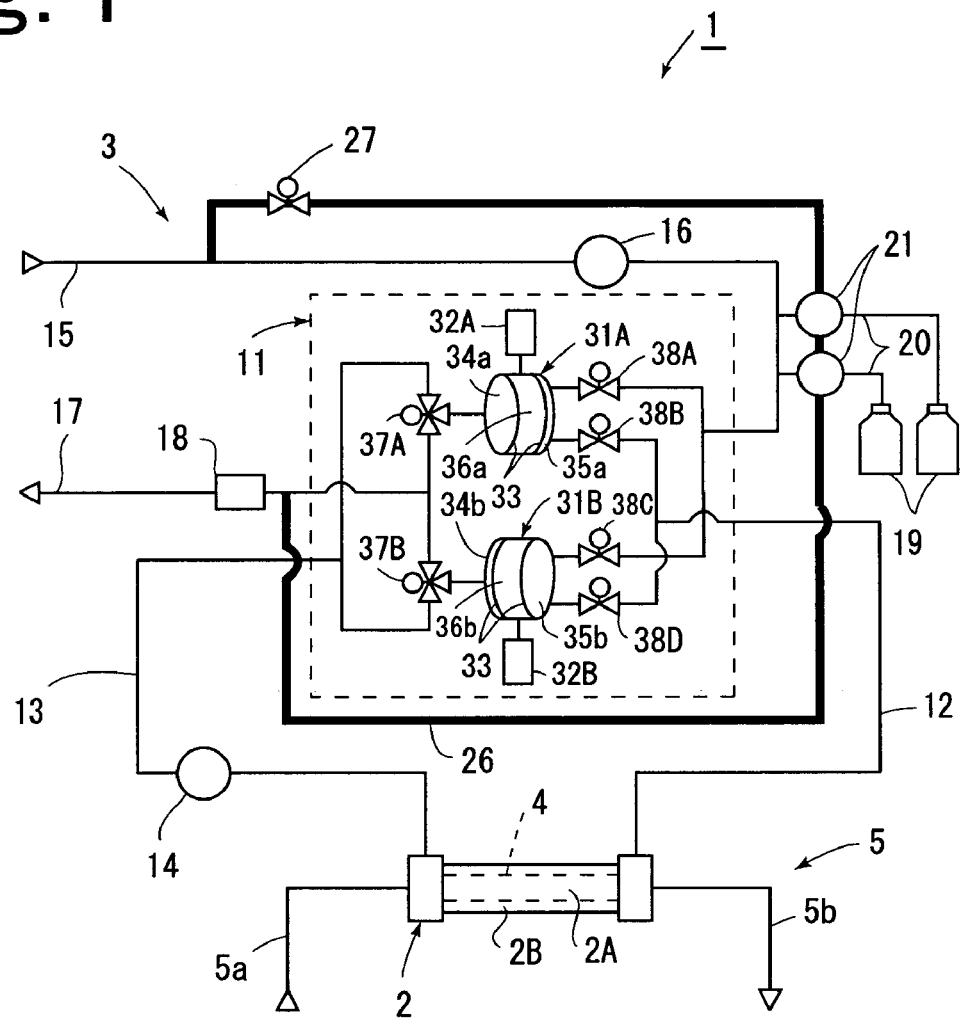
FIG. 1 is a circuit diagram of a dialysis device according to a first embodiment of the invention.

Now, illustrated embodiments will be described. FIG. 1 is a circuit diagram of a dialysis device 1 according to an embodiment of the invention, and the dialysis device 1 includes a dialyser 2, and a dialysis solution circuit 3 and a blood circuit 5 connected to the dialyser 2 for flowing a dialysis solution and for flowing blood, respectively. The dialysis device 1 is controlled by unshown control means.

Many hollow fibers 4 tied into a bundle are provided in the dialyser 2, and blood flows through the hollow fibers 4. FIG. 1 diametrically shows one hollow fiber 4 in the dialyser 2, and the inside of the hollow fiber 4 is a blood chamber 2A, and the outside of the hollow fiber 4 is a dialysis solution chamber 2B.

To the blood chamber 2A, a blood passage 5a connected to a human body for feeding blood to the blood chamber 2, and a blood passage 5b for returning blood to the human body are connected, and blood flows through the blood chamber 2A from the left to the right in FIG. 1.

The dialysis solution circuit 3 includes a dialysis solution supply/discharge means 11 for controlling the amount of new dialysis solution supplied to the dialyser 2 and the amount of used dialysis solution collected from the dialyser 2.

To the dialysis solution supply/discharge means 11, a supply passage 12 for supplying the new dialysis solution to the dialysis solution chamber 2B, and a collection passage 13 for discharging the used dialysis solution from the dialysis solution chamber 2B are connected, and a water supply passage 15 for flowing clean water supplied from an unshown water supply source is also connected.

The used dialysis solution in the collection passage 13 is fed by a collection pump 14 provided in the collection passage 13, and the clean water in the water supply passage 15 is fed to the dialysis solution supply/discharge means 11 by a water supply pump 16 provided in the water supply passage 15.

Further, to the dialysis solution supply/discharge means 11, a waste solution passage 17 for discharging the used dialysis solution from the dialysis solution supply/discharge means 11 to an unshown waste solution tank is connected, and blood leak detection means 18 for detecting blood in the used dialysis solution is provided in the waste solution passage 17.

The dialysis device 1 according to the embodiment is a single-patient-use dialysis device that mixes the clean water flowing through the water supply passage 15 and a dialysis concentrate solution to prepare a dialysis solution, and the dialysis solution circuit 3 includes two concentrate solution supply sources 19 storing sodium chloride (NaCl) and sodium hydrogencarbonate (NaHCO$_3$) that are dialysis concentrate solutions. The concentrate solution supply sources 19 are connected to the water supply passage 15 via concentrate solution supply passages 20, and each concentrate solution supply passage 20 includes a piston pump (see FIG. 2) as a concentrate solution pump 21.

In the embodiment, in order to wash the blood leak detection means 18 and the concentrate solution pump 21, a washing passage 26 is provided branching from an upstream side of the water supply pump 16 in the water supply passage 15 and connected to an upstream position near the blood leak detection means 18 in the waste solution passage 17, and an open/close valve 27 opened and closed by control means is provided in the washing passage 26 on an upstream side of the concentrate solution pump 21.

The dialysis solution supply/discharge means 11 includes a first chamber 31A and a second chamber 31B of the same shape, and the first chamber 31A and the second chamber 31B include silicone oil pumps 32A and 32B, respectively.

The first chamber 31A and the second chamber 31B each include two diaphragms 33, and are partitioned into solution collection chambers 34a and 34b, solution supply chambers 35a and 35b, and variable capacity chambers 36a and 36b therebetween.

The collection passage 13 and the waste solution passage 17 branch to be connected to the solution collection chambers 34a and 34b via first and second three-way valves 37A and 37B, while the supply passage 12 and the water supply passage 15 also branch to be connected to the solution supply chambers 35a and 35b via first to fourth solenoid valves 38A to 38D.

The variable capacity chambers 36a and 36b are filled with silicone oil, and the capacities of the variable capacity chambers 36a and 36b can be varied by increasing and decreasing the amount of silicone oil by the silicone oil pumps 32A and 32B.

Figure 2:
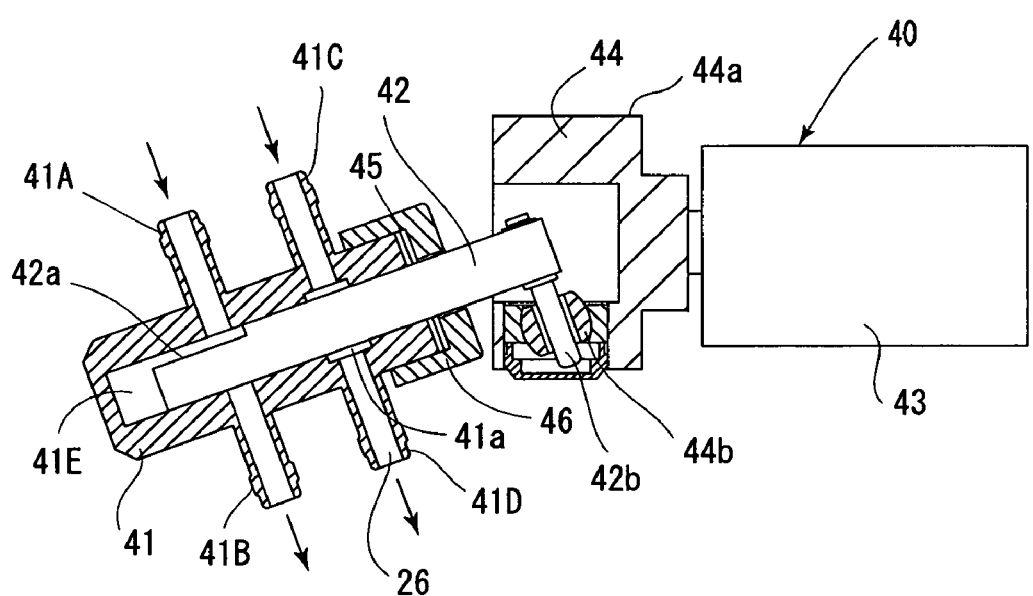
FIG. 2 is a sectional view of a piston pump.

Next, a piston pump 40 used as the concentrate solution pump 21 will be described. As shown in FIG. 2, the piston pump 40 includes a cylinder 41, a piston 42 moving up and down while rotating in the cylinder 41, and a motor 43 for driving the piston 42, and the piston 42 and the motor 43 are connected by a joint mechanism 44.

The joint mechanism 44 includes a cylindrical member 44a secured to a rotation axis of the motor 43, and a spherical bearing 44b provided on an inner wall of the cylindrical member 44a, and the piston 42 is connected to the joint mechanism 44 by passing a pin 42b provided on an end of the piston 42 protruding from the cylinder 41 through a spherical member of the spherical bearing 44b.

On a tip side of the cylinder 41, a suction port 41A communicating with the concentrate solution supply source 19 via the concentrate solution supply passage 20 and a discharge port 41B communicating with the water supply passage 15 via the concentrate solution supply passage 20 are provided.

A notch 42a is provided in a tip of the piston 42. The suction port 41A communicates with a metering chamber 41E formed in the cylinder 41 by the notch 42a just until the piston 42 reaches top dead center, while the discharge port 41B communicates with the metering chamber 41E just until the piston 42 reaches bottom dead center.

Therefore, the concentrate solution is sucked from the suction port 41A until the piston 42 reaches the top dead center, and then the sucked concentrate solution is discharged from the discharge port 41B until the piston 42 reaches the bottom dead center.

Thus, setting the number of revolutions of the motor 43 allows a required amount of solution to be accurately fed. In FIG. 2, the piston 42 is at the bottom dead center in the joint mechanism 44, and the tip side of piston 42 is between the bottom dead center and the top dead center for illustration.

On the motor 43 side of the cylinder 41, a seal member 45 surrounding the piston 42 and a cap member 46 for securing the seal member 45 to the cylinder 41 are provided.

Further, in the embodiment, clean water flowing through the washing passage 26 is flown into and out of a gap between an inner surface of the cylinder 41 and an outer surface of the piston 42 of the piston pump 40 used as the concentrate solution pump 21.

Specifically, a groove 41a surrounding the piston 42 is formed in an inner peripheral surface of the cylinder 41, and an inflow port 41C and an outflow port 41D are formed in communication with the groove 41a. Then, the piston pump 40 is placed in the way of the washing passage 26 by connecting the inflow port 41C to an upstream side and the outflow port 41D to a downstream side.

Therefore, opening the open/close valve 27 allows the clean water from the water supply passage 15 to flow through the inflow port 41C, the groove 41a, and the outflow port 41D to the waste solution passage 17, and the piston 42 moving up and down while rotating allows the clean water to flow into and out of the gap between the inner surface of the cylinder 41 and the outer surface of the piston 42 via the notch 42a.

In the embodiment, two concentrate solution pumps 21 are provided as shown in FIG. 1, and an outflow port 41D of a concentrate solution pump 21 on the upstream side of the washing passage 26 communicates with an inflow port 41C of a concentrate solution pump 21 on the downstream side through the washing passage 26, thus connecting two piston pumps 40 in series.

Figure 3:
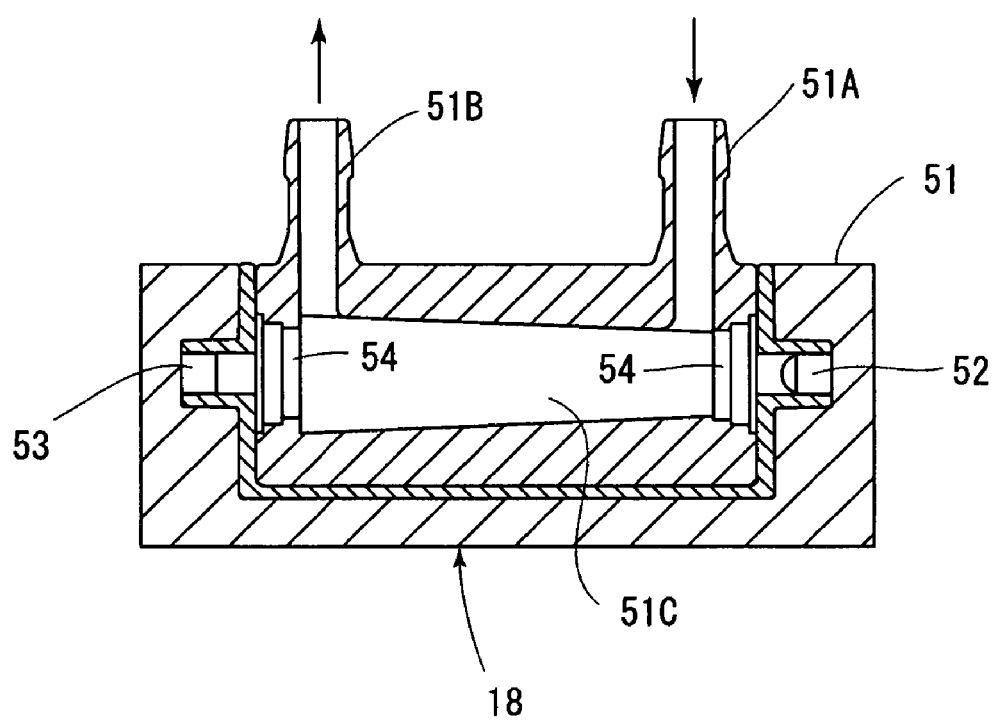
FIG. 3 is a sectional view of blood leak detection means.

Next, the blood leak detection means 18 provided in the waste solution passage 17 has a cylindrical housing 51 as shown in FIG. 3, and a waste solution suction port 51A and a waste solution discharge port 51B connected to the waste solution passage 17 are formed in a peripheral surface of the housing 51. The used dialysis solution flows into the waste solution suction port 51A on the right in FIG. 3, and is discharged out of a waste solution discharge port 51B on the left side.

In the housing 51, a passage 51C that provides communication between the waste solution suction port 51A and the waste solution discharge port 51B are formed, and the passage 51C has a light emitting element 52 at one end and a light receiving element 53 at the other end.

The light receiving element 53 is connected so as to send a light receiving signal to the control means, and the light emitting element 52 and the light receiving element 53 are separated from the passage 51C by transparent plates 54 made of glass or resin so as not to directly contact the used dialysis solution.

When the light emitting element 52 emits light while the used dialysis solution flows through the passage 51C, the light having passed through the used dialysis solution is received by the light receiving element 53, and the light receiving signal is sent to the control means.

At this time, if blood is mixed into the used dialysis solution, transparency of the light changes to reduce the amount of light received by the light receiving element 53, and thus the control means determines the mixture of blood into the used dialysis solution from the reduction in the amount of received light.

A dialysis operation of the dialysis device 1 having the above described configuration will be described.

First, in the dialysis solution supply/discharge means 11, for example, the first three-way valve 37A provides communication between the collection passage 13 and the solution collection chamber 34a of the first chamber 31A, the second three-way valve 37B provides communication between the solution collection chamber 34b of the second chamber 31B and the waste solution passage 17, the first solenoid valve 38A and the fourth solenoid valve 38D are closed, the second open/close valve 38B is opened to provide communication between the solution supply chamber 35a of the first chamber 31A and the supply passage 12, and the third open/close valve 38C is opened to provide communication between the water supply passage 15 and the solution supply chamber 35b of the second chamber 31B.

In this state, operations of the water supply pump 16 and the concentrate solution pump 21 cause the clean water and each concentrate solution to flow into the solution supply chamber 35b through the water supply passage 15 to prepare a new dialysis solution in the solution supply chamber 35b.

Then, the clean water and each concentrate solution flowing into the solution supply chamber 35b moves the diaphragm 33 to the left end in the drawing (the state in FIG. 1). This causes the used dialysis solution stored in the solution collection chamber 34b to be discharged, and the dialysis solution is drained from a waste solution port via the waste solution passage 17.

On the other hand, an operation of the collection pump 14 causes the used dialysis solution to flow from the dialysis solution chamber 2B of the dialyser 2 into the solution collection chamber 34a via the collection passage 13, which moves the diaphragm 33 to the right end in the drawing (the state in FIG. 1). This causes a new dialysis solution stored in the solution supply chamber 35a to be discharged, and the dialysis solution is supplied to the dialysis solution chamber 2B via the supply passage 12.

At this time, the silicone oil pump 32A of the first chamber 31A in which the used dialysis solution is collected is operated to reduce the capacity of the variable capacity chamber 36a by a predetermined amount. This allows an increase in the capacity of the solution collection chamber 34a, and a solution corresponding to the amount of increase is removed.

Then, when the state in FIG. 1 is obtained, the control means operates so as to control the first and second three-way valves 37A and 37B and the first to fourth solenoid valves 38A to 38D, provide communication between the solution collection chamber 34a and the waste solution passage 17, the solution supply chamber 35a and the water supply passage 15, the solution collection chamber 34b and the collection passage 13, and the solution supply chamber 35b and the supply passage 12 to switch connecting states of the first chamber 31A and the second chamber 32B, and continuously supply a new dialysis solution to the dialyser 2 and collect the used dialysis solution.

During the above described dialysis operation, the following problem occurs in the concentrate solution pump 21.

Specifically, in the concentrate solution pump 21 (the piston pump 40), the piston 42 moves up and down to dispense the concentrate solution, and at this time, a trace amount of concentrate solution flows into the gap between the sliding portions of the inner surface of the cylinder 41 and the outer surface of the piston 42.

Such a concentrate solution thus having flown into the gap between the cylinder 41 and the piston 42, dries and is crystallized therein, thus impairing sliding performance between the cylinder 41 and the piston 42.

Thus, in this embodiment, the clean water from the water supply passage 15 is flown into the sliding portions of the cylinder 41 and the piston 42 via the washing passage 26 to prevent drying and crystallization of the concentrate solution.

For the timing when the open/close valve 27 is opened and closed, in the embodiment, the amount of clean water fed to the solution supply chambers 35a and 35b by the water supply pump 16 is set to be larger than the amount of used dialysis solution fed to the solution collection chamber 34a and 34b by the collection pump 14.

Thus, a predetermined amount of dialysis solution is prepared in the solution supply chambers of one pair of chambers to which the water supply passage 15 is connected, and after a predetermined time period, a predetermined amount of used dialysis solution is collected into the solution collection chambers of the other pair of chambers to which the collection passage 13 is connected.

Then, the connection state is switched by the solenoid valves 38A to 38D, and the above described one pair of solution supply chambers communicate with the supply passage 12 to supply a new dialysis solution to the dialyser 2.

In the embodiment, the open/close valve 27 is opened in the time period between when a new dialysis solution is prepared in the above described one pair of solution supply chambers to which the water supply passage 15 is connected and when connection of the pair of solution supply chambers is switched to the supply passage to start supply of the new dialysis solution to the dialyser 2.

Therefore, the open/close valve 27 is opened intermittently or regularly during the dialysis operation.

When the clean water and the concentrate solution are supplied to the solution supply chambers 35a and 35b to prepare a new dialysis solution as in the single-patient-use dialysis device according to the embodiment, it is necessary not only to dispense the clean water and the concentrate solution but also to flow the clean water at a constant flow rate into the solution supply chambers 35a and 35b with agitation to be uniform.

If the open/close valve 27 is opened during such preparation of the dialysis solution, the clean water branches from the water supply passage 15 to the washing passage 26, thus reducing the flow rate of the clean water supplied through the water supply passage 15 to reduce an agitation effect in the solution supply chambers 35a and 35b.

Thus, in the embodiment, the open/close valve 27 is opened at the above described intervals to supply the clean water to the washing passage 26 without impairing preparation of the dialysis solution in the solution supply chamber. Further, during the preparation of the dialysis solution, that is, during the operation of the concentrate solution pump 21, water supply pressure from the water supply source does not continuously acts on the gap between the inner surface of the cylinder 41 and the outer surface of the piston 42, and thus no inflow clean water leak into the metering chamber 41E in the cylinder 41 to dilute the concentrate solution.

With the open/close valve 27 being closed, the clean water is not discharged from the washing passage 26 and the groove 41a in the cylinder 41 is stored. Thus, for the operation of the piston pump 40 during the dialysis operation, the piston 42 moves up and down while rotating in the groove 41a surrounding the piston 42, and the stored clean water adheres to the outer surface of the piston 42, thereby preventing drying of the sliding portions of the cylinder 41 and the piston 42.

Next, the blood leak detection means 18 has a problem that an ingredient such as protein of the used dialysis solution adheres to the transparent plate 54 of the blood leak detection means 18 and is built up over time to reduce the amount of light emitted to the passage 51C by the light emitting element 52 and the amount of light received by the light receiving element 53 to reduce detection accuracy.

In this connection, according to the embodiment, the washing passage 26 is connected to the upstream position near the blood leak detection means 18 to flow the clean water and wash the transparent plate 54 during the dialysis operation at regular intervals, thereby preventing buildup of protein.

Figure 4:
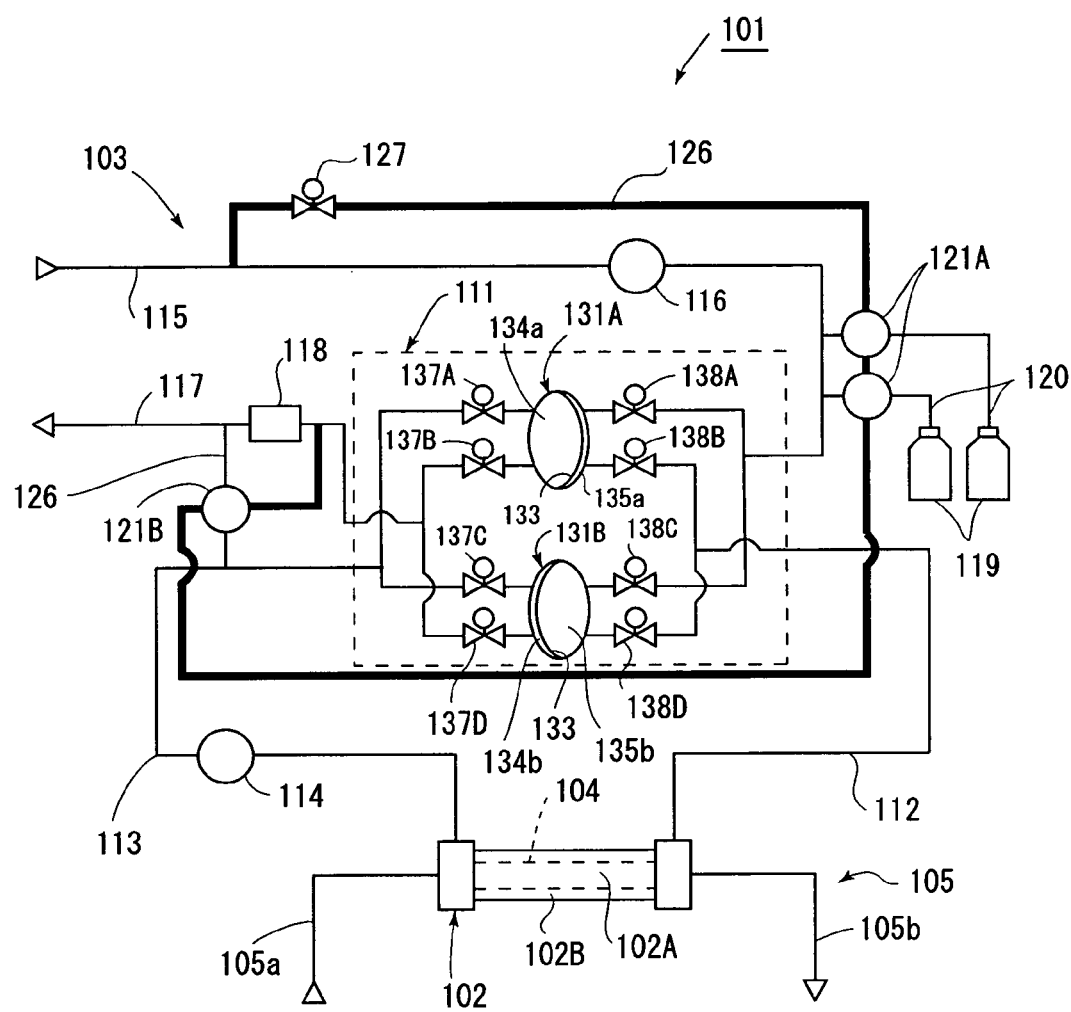
FIG. 4 is a circuit diagram of a dialysis device according to a second embodiment of the invention.

Next, a second embodiment according to the invention will be described. FIG. 4 is a circuit diagram of a dialysis device 101 according to the embodiment, and in FIG. 4, components in common with those in the first embodiment are denoted by reference numerals with 100 added to the reference numerals in the first embodiment.

The dialysis device 101 is a single-patient-use dialysis device like the dialysis device 1 according to the first embodiment, includes a dialyser 102, and a dialysis solution circuit 103 and a blood circuit 105 connected to the dialyser 102 for passing a dialysis solution and for passing blood, respectively, and is controlled by unshown control means.

The dialysis device 101 according to this embodiment has a different configuration of a dialysis solution supply/discharge means 111 in the dialysis solution circuit 103 from the dialysis solution supply/discharge means 11 in the first embodiment, and the difference will be now mainly described.

The dialysis solution supply/discharge means 111 includes a first chamber 131A and a second chamber 131B of the same shape, the first chamber 131A and the second chamber 131B each have one diaphragm 133, and are partitioned into solution collection chambers 134a and 134b and solution supply chambers 135a and 135b.

A collection passage 113 and a waste solution passage 117 branch to be connected to solution collection chambers 134a and 134b via first to fourth solenoid valves 137A to 137D, while a supply passage 112 and a water supply passage 115 also branch to be connected to solution supply chambers 135a and 135b via fifth to eighth solenoid valves 138A to 138D.

In the embodiment, one end of a washing passage 126 is connected to a downstream side of a collection pump 114 of the collection passage 113 and an upstream side of a branch point to the first solenoid valve 137A and the third solenoid valve 137C, and the other end thereof is connected to a downstream side of a confluence of the second solenoid valve 137B and the fourth solenoid valve 137D of the waste solution passage 117. A extraction pump 121B is provided in the way of the washing passage 126 to allow a used dialysis solution to be fed from the collection passage 113 to the waste solution passage 117.

Like a concentrate solution pump 121A, a piston pump 40 in FIG. 2 is used as the extraction pump 121B, and the collection passage 113 side of the water removal passage 126 is connected to a suction port 41A and the waste solution passage 117 side is connected to a discharge port 41B.

In the embodiment, the extraction pump 121B is connected in the way of the washing passage 126 and to a downstream side of the two concentrate solution pumps 121A and 121A in the washing passage 126 to provide communication between an inflow port 41C of the extraction pump 121B and an outflow port 41D of the concentrate solution pump 121A on the downstream side, and provide communication between the outflow port 41D and the waste solution passage 117 on the upstream side of a blood leak detection means 118.

Thus, an open/close valve 127 is opened to allow clean water discharged from the outflow port 41D of the concentrate solution pump 121A on the downstream side to be discharged into the waste solution passage 117 via the inflow port 41C, a groove 41a in a cylinder 41, and the outflow port 41D of the extraction pump 121B.

As described above, the dialysis device 101 configured as described above according to the second embodiment differs from the dialysis device 1 according to the first embodiment in that the first to fourth solenoid valves 137A to 137D are used to switch connection of the solution collection chambers 134a and 134b to the collection passage 113 and the waste solution passage 117, and that an water removal operation is performed by the extraction pump 121B, but essential dialysis operations are common and descriptions thereof will be omitted.

When the water removal operation is performed by the extraction pump 121B, a motor 43 of the piston pump 40 used as the extraction pump 121B is rotated by a predetermined amount while one of the solution collection chambers 134a and 134b collects the used dialysis solution, and a predetermined amount of used dialysis solution flowing in the collection passage 113 is discharged to the waste solution passage 117 without passing through the solution collection chambers 134a and 134b.

When the piston pump 40 is used as the extraction pump 121B as in the dialysis device 101, the following problem occurs.

Specifically, when the used dialysis solution is fed by the extraction pump 121B during the dialysis operation, a trace amount of used dialysis solution flows into the gap between the sliding portions of the inner surface of the cylinder 41 and the outer surface of the piston 42, like when the concentrate solution is fed by the concentrate solution pump 121A.

From the used dialysis solution having flown into the gap, calcium carbonate is deposited by friction resulting from sliding, which may impair sliding performance between the cylinder 41 and the piston 42 and cause adhesion therebetween.

In the embodiment, for the piston pump 40 not only as the concentrate solution pump 121A but also as the extraction pump 121B, the open/close valve 127 is opened at a similar timing as in the first embodiment, the clean water is flown from the inflow port 41C into the gap between the inner surface of the cylinder 41 and the outer surface of the piston 42, and then the clean water is discharged from the outflow port 41D to wash off the deposited calcium carbonate. This prevents buildup of the deposited calcium carbonate, and impairment of sliding performance between the cylinder 41 and the piston 42.

With the open/close valve 127 being closed, the clean water is not discharged from the washing passage 126 and the groove 41a in the cylinder 41 but is stored, and for the operation of the piston pump 40 during the dialysis operation, the piston 42 moves up and down while rotating in the groove 41a surrounding the piston 42, and the deposited calcium carbonate is scraped off into the groove 41a.

Next, when the open/close valve 127 is opened, the clean water from the inflow port 41C flows into the gap between the inner surface of the cylinder 41 and the outer surface of the piston 42 for washing, and the clean water stored in the groove 41a is flown out of the outflow port 41D, thus preventing buildup of calcium carbonate on the sliding portions of the cylinder 41 and the piston 42.

In the second embodiment, the extraction pump 121B is placed so as to be connected to the downstream side of the concentrate solution pump 121A in the washing passage 126, but may be connected to the upstream side. Further, the extraction pump 121B and the concentrate solution pump 121A may be connected to different washing passages 126, or only one of them may be connected to the washing passage 126.

What is claimed is:

1. A dialysis device comprising:
    a solution supply chamber for supplying a new dialysis solution to a dialyser via a supply passage;
    a solution collection chamber for collecting a used dialysis solution from the dialyser via a collection passage;
    a water supply passage for supplying clean water to said solution supply chamber;
    a waste solution passage for discharging the used dialysis solution from said solution collection chamber; and
    a piston pump that moves a piston up and down in a cylinder to feed a solution,
    wherein said dialysis device further comprises: a washing passage that provides communication between said water supply passage and said waste solution passage to flow said clean water therethrough; and an open/close valve for opening and closing said washing passage, and said piston pump is at least one of a concentrate solution pump that sucks a dialysis concentrate solution from a concentrate solution supply source and supplies the sucked dialysis concentrate solution to said solution supply chamber, and an extraction pump that sucks the used dialysis solution from said collection passage and discharges the sucked used dialysis solution to said waste solution passage,
    the cylinder of said piston pump has an inflow port for flowing a solution into a gap between an inner surface of the cylinder and an outer surface of the piston, and an outflow port for flowing the solution out of the gap, and the inflow port and the outflow port are connected in the way of said washing passage, and
    said open/close valve is intermittently opened during a dialysis operation to flow the clean water in the water supply passage through the gap between the inner surface of the cylinder and the outer surface of the piston.

2. The dialysis device according to claim 1, wherein said washing passage provides communication between a plurality of piston pumps in series.

3. The dialysis device according to claim 1, wherein two pairs of solution supply chambers and solution collection chambers are provided, and said two pairs of solution supply chambers and solution collection chambers are configured so that when the clean water and the concentrate solution are supplied to one pair of solution supply chambers to prepare a new dialysis solution, the used dialysis solution is discharged from the pair of solution collection chambers, while a new dialysis solution is supplied from the other pair of solution supply chambers to the dialyser and the used dialysis solution from the dialyser is collected into the pair of solution collection chambers, and
    said open/close valve is opened in the time period between when the new dialysis solution is prepared in said one pair of solution supply chambers and when supply of the new dialysis solution from the pair of solution supply chambers to the dialyser is started.

* * * * *